United States Patent
Bialczak

[11] 3,971,663
[45] July 27, 1976

[54] LIGHT-SENSITIVE DIAZOTYPE WITH YELLOW DIAZO COUPLERS

[76] Inventor: Edward C. Bialczak, 3 Cornfield Lane, Guilford, Conn. 06437

[22] Filed: Apr. 11, 1974

[21] Appl. No.: 460,130

[52] U.S. Cl. .................... 96/91 R; 96/49; 96/75; 260/558 R; 260/558 A
[51] Int. Cl.² .......................... G03C 1/58
[58] Field of Search .............. 96/91 R, 75, 49

[56] References Cited
UNITED STATES PATENTS

| | | | |
|---|---|---|---|
| 1,989,065 | 1/1935 | Schmidt et al. | 96/91 R |
| 2,423,460 | 7/1947 | McQueen | 96/91 R |
| 2,531,004 | 11/1950 | Slifkin | 96/91 R |
| 2,537,001 | 1/1951 | VonGlahn et al. | 96/91 R |
| 2,551,570 | 5/1951 | VonGlahn et al. | 96/91 R |
| 2,552,355 | 5/1951 | VonGlahn et al. | 96/91 R |
| 3,386,827 | 6/1968 | Aebi et al. | 96/91 R |
| 3,558,318 | 1/1971 | Sheehan | 96/91 R |
| 3,694,247 | 9/1972 | Desjarlais | 96/91 R |
| 3,708,301 | 1/1973 | Muller | 96/91 R |
| 3,836,369 | 9/1974 | Looney et al. | 96/91 R |

FOREIGN PATENTS OR APPLICATIONS

| | | | |
|---|---|---|---|
| 937,510 | 9/1963 | United Kingdom | 96/91 R |
| 983,662 | 2/1965 | United Kingdom | 96/91 R |

OTHER PUBLICATIONS

Dinaburg, M. S., "Photosensitive Diazo Compounds," The Focal Press, 1964, pp. 106–109.

Kosor, Jr., "Light–Sensitive Systems," Wiley & Sons, 1965, pp. 241–243.

*Primary Examiner*—Charles L. Bowers, Jr.
*Attorney, Agent, or Firm*—Mason, Kolehmainen, Rathburn & Wyss

[57] ABSTRACT

A light-sensitive diazotype material comprising a base support having a coating thereon which comprises a light-sensitive diazonium compound and a coupling component having the general formula

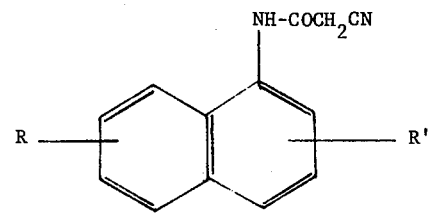

wherein R is hydrogen, a lower alkyl radical, halogen or aryl, and R' is hydrogen or $SO_3M$ wherein M is a monovalent cation.

4 Claims, No Drawings

LIGHT-SENSITIVE DIAZOTYPE WITH YELLOW DIAZO COUPLERS

This invention relates to diazo couplers or coupling components for producing yellow images when reacted with a light-sensitive diazo compound. More particularly, it relates to couplers which react rapidly with diazo compounds and have good shelf life and which can be used in the dry diazo process disclosed in the Parker U.S. Pat. No. 3,578,452, and to diazo compositions containing such couplers.

BACKGROUND OF THE INVENTION

Diazo reproduction processes based on light-sensitive diazonium compounds and their ability to form azo dyes with a coupling component under proper pH conditions are generally well known. The various techniques for carrying out the development include the moist or semi-moist process, the dry or ammonia process, and the thermal process. The diazo copying materials adapted for the moist process are referred to as one-component materials since they contain only the light-sensitive diazo compounds, and the coupling component is provided in a separate buffered developing solution which is applied at the time of development. Diazotype materials developed in an atmosphere of water vapor and ammonia gas are generally referred to as two-component materials since they contain both the diazonium salt and the coupling component stabilized against premature coupling in an acidic medium. In the thermal systems heat is employed to release the alkaline agents which are coated on the copy material along with the diazonium salt and the coupler. Each of these systems provides a successful copying process but not without certain disadvantages that limit their utility which would otherwise permit diazo copying to enjoy more widespread application as a reproduction medium.

Two-component materials have found wide use in the reproduction of engineering drawings. The process of developing with ammonia gas and water vapor is fast and essentially dry. Ammonia vapor readily penetrates into the exposed copy sheet surface and permeates the light-sensitive coating containing acid stabilizers, shifting the pH of the coating to the alkaline side. Any excess of ammonia enhances the rate of the reaction and volatilizes from the copy sheet without leaving a residue. One of the major objections to the use of ammonia in developing diazotype materials is the strong odor of ammonia in the copying area as well as the tendency for the odor to linger on the copies themselves. Installation of ammonia reproduction machines requires venting of the equipment to the outdoors to remove the toxic vapors. This limits the installation of the equipment to sites where the venting may be conveniently accomplished. The equipment is further complicated by the need for a gas-developing chamber to contain the ammonia gas and water vapor and the other appurtenances required for feeding the developing ingredients to the chamber. The equipment, understandably, is not well suited for office installations.

The one-component systems have effectively eliminated the odor problem by applying liquid developers directly to the copy sheet. Reproduction equipment for use with the one-component type papers requires heating elements to dry the copy sheet after development. Thermal systems, while offering the advantages of dry copying without the presence of undesirable odors, suffer in that the copying materials themselves may lack stability. The machines are objectionable because of the amount of heat given off into the surrounding work area.

Attempts have been made to simplify the processing of diazotype materials, particularly the two-component types, by using alkaline liquids applied directly to the latent image bearing surface. These prior attempts to eliminate the complexities of gaseous development have been unsuccessful for a number of reasons.

By the procedure of the Parker U.S. Pat. No. 3,578,452 it has been possible to use a liquid organic amine as the developer for two-component diazotype materials and produce dry copies directly from the developing step. Development is accomplished by supplying controlled amounts of a concentrated developer solution, preferably comprising an aliphatic amine in a solvent, to a developing region and then passing an exposed diazotype paper through the developing region. At the developing region the controlled small amount of developer liquid is applied directly to the surface bearing the latent diazo image to effectively develop the azo image and produce prints which emerge dry, odor-free and ready for use.

Within the developing region the limited quantity of developer liquid is applied under pressure, thus being spread out uniformly over its entire surface in a layer having a thickness of about 1 micron, which is sufficient to cause rapid image development. The azo dye image is found to develop evenly and uniformly everywhere across the copy area, indicating the effectiveness of the method. A visible, readable image begins to form instantaneously as the copy emerges from the developing region and rapidly increases in density, attaining its maximum image density well within one minute and usually within 15 seconds. Understandably, the rate at which maximum density is reached will depend in part on the couplers and diazonium compounds used in making the copy sheets.

Although the color of the azo dye image which is obtained in any given instance depends primarily on the coupling components and the diazonium compounds which are employed, coupling components are often generally described as being couplers of a given color — the color being the color of the dye which is usually obtained when the particular coupler in question couples with a diazonium compound. For example, couplers such as monohydric phenols, catechols, catechol derivatives, resorcinols, resorcinol derivatives, diketones, acetoacetic acid derivatives, acetonitriles, cyanacetylamides and the like, usually result in yellow, orange, sepia, brown, red or maroon azo dyes. Thus, couplers from such classes of materials are conveniently referred to as yellow, orange, sepia, brown, red, or maroon couplers. On the other hand, couplers such as naphthoic acid derivatives, dioxynaphthalene derivatives, pyronones, hydroxypyronones, and the like, usually result in blue or violet azo dyes, and thus are conveniently referred to as blue or violet couplers.

One group of highly useful coupling components are the yellow couplers, since the dyes obtained from these couplers usually have actinic adsorption characteristics which permit their use as the sole coupler in a diazo composition which is employed to prepare diazotype "masters" or intermediates, and since couplers from this group can often be employed as shading components when used in conjunction with another coupler or couplers. As indicated above, compounds containing active methylene groups, compounds such as acetonitriles, derivatives of acetonitriles, and the like, have been employed as yellow couplers in diazo compositions, cf. for example, U.S. Pat. Nos. 1,989,065; 2,531,004; 2,537,001; 2,537,106 and 3,558,318; yet, a number of these active-methylene types of couplers have exhibited a tendency, when employed in two-component diazo compositions, to precouple with the diazonium compound which is present in said compositions during storage even in the presence of the stabilizers which are usually employed. This tendency to precouple prior to exposure and development has limited the use of these materials somewhat, since even a slight amount of precoupling can result in the formation of an azo dye in those areas of the diazotype material which are the background or "cleared" areas of the diazotype print. In addition to this tendency to precouple, a number of these prior art, active-methylene types of couplers also result, upon coupling, in dyes which have an undesirable reddish blue.

Well known among the yellow couplers are such compounds as cyanoacetmorphilide and cyanoacetanilide. The former is very slow coupling whereas the latter is extremely fast but results in materials with a greatly reduced shelf life. Ideally, a coupler should be reasonably faster than the known slow reacting yellow coupler without suffering the detriment of poor shelf life.

SUMMARY OF THE INVENTION

The couplers of this invention have properties which are particularly suitable for the amine development procedure described above. They react rapidly with diazo compounds at the proper pH range, form high density images comparable to those obtained by ammonia development, form diazo prints of good contrast and image shade, and have relatively long shelf life required for commercial use.

The couplers which comprise this invention have the general formula

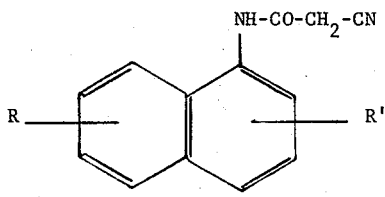

wherein R is hydrogen, a lower alkyl group containing one to six carbon atoms, a halogen, or an aryl radical, and R' is hydrogen or $SO_3M$ where M is a monovalent cation. These compounds are preferably produced from the corresponding alpha-naphthylamines

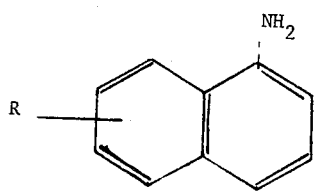

by reaction with an alkyl cyanoacetate at elevated temperature.

Optionally, the cyanoacetnaphthamide produced by the foregoing procedure can be made water-soluble by sulfonation with fuming sulfuric acid or chlorosulfonic acid.

The diazo coating composition is preferably of the two-component type containing both the cyanoacetnaphthylamine coupler and the light-sensitive diazo compound in a mixture of organic solvents. The composition is coated on paper or an organic film such as polyethylene terephthalate (Mylar). After exposure to a pattern of light, the image is developed by application of an organic amine developer as described in the Parker U.S. Pat. No. 3,578,452.

Light-sensitive diazo compositions of the two-component type which contain yellow couplers as described above exhibit excellent shelf life and are less susceptible to precoupling during storage than are prior diazo compositions. The yellow couplers which are employed in the diazo compositions of this invention exhibit, upon development, a high coupling rate with the diazonium compounds employed in such compositions, with a significant reduction in the tendency to precouple. The azo dyes obtained from these couplers are yellow or yellow-green in shade.

DETAILED DESCRIPTION OF THE INVENTION

The couplers which comprise this invention have the general formula given above, wherein R can represent methyl, ethyl, propyl, isopropyl, butyl, isobutyl, amyl, isoamyl, hexyl, chloro, bromo, fluoro, iodo, phenyl, p-tolyl, o-tolyl, m-tolyl, xylyl and similar radicals. The reaction of the substituted alpha-naphthylamine and the alkyl cyanoacetate is usually conducted at elevated temperature without a solvent, although a solvent such as an alcohol, hydrocarbon or chlorinated hydrocarbon, boiling between 80° and 150°C., may be preferable. The reaction product is rather insoluble in such solvents and crystallizes out as the reaction proceeds, thus simplifying purification and isolation of the coupler.

The diazo coating compositions contain a coupler as described above with a light-sensitive diazonium salt, usually in the form of a zinc chloride double salt. The light-sensitive diazonium compounds which can be employed in preparing the light-sensitive diazo compositions of the present invention are any of the numerous light-sensitive diazonium compounds which are available in the prior art, and the particular light-sensitive diazonium compound which is employed is not critical in the practice of this invention. Illustrative of such compounds are the stabilized salts of diazonium derivatives of a p-phenylenediamine, for example, stabilized salts of diazonium derivatives of such compounds as
N-methyl-p-phenylenediamine,
N-ethyl-p-phenylenediamine,
N-hydroxyethyl-p-phenylenediamine,
N,N-dimethyl-p-phenylenediamine,
N,N-diethyl-p-phenylenediamine,
N,N-dipropyl-p-phenylenediamine
N-methyl-N-(beta-hydroxyethyl)-p-phenylenediamine,
N-ethyl-N-(beta-hydroxyethyl)-p-phenylenediamine,
N-(beta-hydroxyethyl)-p-phenylenediamine,
N-butyl-N-(beta-hydroxyethyl)-p-phenylenediamine,
N,N-di(beta-hydroxyethyl)-p-phenylenediamine,
N-benzyl-N-ethyl-p-phenylenediamine, N-ethyl-2-methyl-4-aminoaniline,
N,N-dimethyl-2-methyl-4-aminoaniline,
N,N-dimethyl-3-methyl-4-aminoaniline,
N,N-diethyl-3-methyl-4-aminoaniline,
N-ethyl-N-(beta-hydroxyethyl)-3-methyl-4-aminoaniline,
N-cyclohexyl-2-methoxy-4-aminoaniline,
N,N-di(beta-hydroxyethyl)-3-methyl-4-aminoaniline,
2,5-diethoxy-4-morpholinoaniline,
2,5-dimethoxy-4-morpholinoaniline,
2,5-dibutoxy-4-morpholinoaniline,
2,5-diisopropoxy-4-morpholinoaniline,
2,5-diethoxy-4-piperidinoaniline,
2,5-dimethoxy-4-piperidinoaniline,
N-benzyl-2,5-diethoxy-4-aminoaniline,
2,6-dimethyl-4-morpholinoaniline,
2,6-diethyl-4-morpholinoaniline,
2,6-dimethyl-4-piperidinoaniline.

Mixtures of light-sensitive diazonium compounds can be employed in the practice of the present invention without departing from the scope thereof, and that other couplers can be employed in conjunction with the yellow couplers hereinbefore described in preparing diazo compositions in accordance with the present invention without departing from the scope thereof. In addition, the light-sensitive diazo compositions of this invention can also comprise any of the additional components which are often employed in such compositions, such as stabilizers, preservatives, anti-oxidants, extenders, inhibitors, color intensifiers, and the like.

The various components of the light-sensitive diazo-compositions of this invention are usually dissolved in an organic solvent system, and the resulting solution is then coated by conventional coating techniques onto a suitable base support. The base supports which can be employed are any of those commonly used as support materials in the photographic and copying arts, such as paper, cloth, films and the like. Illustrative of the films which can be employed are films such as cellulose ether films, cellulose ester films (e.g. cellulose acetate and cellulose acetate butyrate), polyester films (e.g. polyethylene terephthalate), and the like. Upon drying, the base support which has been coated with a light-sensitive diazo composition of this invention results in a light-sensitive diazotype material having improved shelf-life stability.

When one of the couplers which has been herein described is the sole coupler present in the light-sensitive diazo composition employed to prepare such diazotype materials, these materials result, upon exposure and development, in a diazotype print having a yellow or greenish-yellow image and a clear background; and such colors are preferred over reddish-yellow shades in certain applications, such as color-proofing.

The invention is described in detail by means of the following examples. It will be understood by those skilled in the art that various modifications in materials and operating conditions can be made within the disclosure of this application.

EXAMPLE 1

One mole (143 g.) of alpha-aminonaphthalene and one mole (113 g.) of ethyl cyanoacetate were heated under reflux for 24 hours. The warm reaction product was poured on ice-hydrochloric acid and the mixture was extracted with methylene chloride. The extract was washed with dilute hydrochloric acid, water and dilute alkali, then concentrated. The precipitate of N-alpha-naphthylcyanoacetamide was crystallized from methanol and methanol-methylene chloride; m.p. 180°–181°C. It has the formula alpha-$C_{10}H_7$-$NHCOCH_2CN$

EXAMPLE 2

Ten grams of N-alpha-naphthylcyanoacetamide was added to 20 g. of 20% fuming sulfuric acid at 20°C. During the addition, the temperature rose to 50°C. After one hour at 50°C. the reaction mixture was poured on ice. The precipitate of cyanoacetamidonaphthalenesulfonic acid was dissolved in 5% sodium hydroxide solution and the solution was filtered and then neutralized with dilute hydrochloric acid to precipitate the purified alpha-cyanoacetamidonaphthalene-sulfonic acid.

Aqueous solutions of water-soluble salts can be produced by dissolving alpha-cyanoacetamidonaphthalenesulfonic acid in dilute (e.g. 1–10%) sodium hydroxide, potassium hydroxide, or ammonium hydroxide solutions, or in dilute aqueous solutions of amines such as methylamine, trimethylamine, ethanolamine, ethylamine, morpholine, diethanolamine and the like. These aqueous solutions of the sulfonic acid salts can be used in preparing aqueous diazotype coating compositions.

EXAMPLE 3

A diazo coating composition was produced from the following materials:

| | |
|---|---|
| Acetone | 60 ml. |
| Methanol | 20 ml. |
| 2-Methoxyethyl acetate | 20 ml. |
| Cellulose acetate (½ second) | 10 grams |
| Sulfosalicylic acid | 0.3 grams |
| Thiourea | 1.0 grams |
| N-alpha-naphthylcyanoacetamide | 2.0 grams |
| 2,5-Diethoxy-4-morpholino-benzenediazonium fluoborate | 1.8 grams |

The composition was coated on cellulose acetate film by the dip coating method. The resulting diazotype material, after exposure to a light pattern, was developed with ammonia vapors and produced a yellow image, suitable as an intermediate for photocopying with light from a mercury vapor lamp.

EXAMPLE 4

A diazo coating composition was made from the following materials:

| | |
|---|---|
| Methyl ethyl ketone | 800 ml. |
| 2-Methoxyethyl acetate | 200 ml. |
| Cellulose acetate propionate (½ second) | 90 g. |
| Sulfosalycilic acid | 3 g. |
| Stannic chloride pentahydrate | 4 g. |
| Thiourea | 4 g. |
| 4-Bromo-3,5-resorcylic acid | 2 g. |
| N-alpha-naphthylcyanoacetamide | 20 g. |
| 3,5-Diethoxy-4-morpholino-benzenediazonium fluoborate | 20 g. |
| Syloid - 244 (silica) (Davison Chemical Co.) | 4 g. |

The first three ingredients were mixed together until the cellulose acetate propionate was completely dissolved (about 30–45 minutes). Then, the remaining ingredients were added to the solution with stirring for 30 minutes to insure complete solution. The resulting solution was coated on polyethylene terephthalate film. After exposure to a light pattern and development with an alkanolamine, in accordance with the method described in U.S. Pat. No. 3,446,620, it gave a sepia image.

EXAMPLE 5

A diazotype paper was prepared with the following sensitizing solution:

| | |
|---|---|
| Water | 600 ml. |
| Diethylene glycol | 40 ml. |
| Citric acid | 20 g. |
| Zinc chloride pentahydrate | 50 g. |
| Isopropyl alcohol | 10 ml. |
| Alpha-cyanoacetamidonaphthalenesulfonic sodium salt | 40 g. |
| 2,5-Diethoxy-4-morpholino-benzenediazonium fluoborate | 36 g. |
| Thiourea | 15 g. |
| Water to make | 1 liter |

The solution was coated on sulphite paper in an amount of 15 g. per square meter. After exposure to a light pattern, the resulting image was developed with ammonia vapor, producing a yellow-green image.

I claim:

1. A light-sensitive diazotype material comprising a base support having an acid stabilized coating thereon which comprises a light-sensitive diazonium compound and a coupling component having the general formula

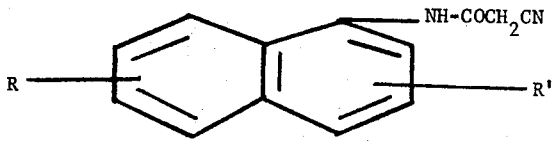

wherein R is hydrogen, a lower alkyl radical, halogen or aryl, and R' is hydrogen or SO$_3$M wherein M is a monovalent cation.

2. A diazotype material as defined in claim 1 wherein R and R' are hydrogen.

3. A diazotype material as defined in claim 1 wherein R is lower alkyl and R' is hydrogen.

4. A diazotype material as defined in claim 1 wherein R is hydrogen and R' is SO$_3$M.

* * * * *